(12) United States Patent
Hoss et al.

(10) Patent No.: US 10,327,677 B2
(45) Date of Patent: Jun. 25, 2019

(54) ANALYTE SENSORS WITH A SENSING SURFACE HAVING SMALL SENSING SPOTS

(75) Inventors: Udo Hoss, Castro Valley, CA (US); Phu Le, Dublin, CA (US); Yi Wang, San Ramon, CA (US); Frank David Fujimoto, Fremont, CA (US); Suyue Qian, Fremont, CA (US); Lam Tran, Vallejo, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1389 days.

(21) Appl. No.: 13/315,034

(22) Filed: Dec. 8, 2011

(65) Prior Publication Data

US 2012/0150005 A1    Jun. 14, 2012

Related U.S. Application Data

(60) Provisional application No. 61/421,371, filed on Dec. 9, 2010.

(51) Int. Cl.
*A61B 5/05* (2006.01)
*A61B 5/145* (2006.01)
*A61B 5/1473* (2006.01)
*C12Q 1/00* (2006.01)

(52) U.S. Cl.
CPC ........ *A61B 5/14532* (2013.01); *A61B 5/1473* (2013.01); *C12Q 1/001* (2013.01); *C12Q 1/006* (2013.01)

(58) Field of Classification Search
CPC . A61B 5/1468; A61B 5/1473; A61B 5/14532; C12Q 1/54; C12Q 1/006; C12Q 1/001
See application file for complete search history.

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,593,852 A | 1/1997 | Heller et al. |
| 6,071,391 A | 6/2000 | Gotoh et al. |

(Continued)

FOREIGN PATENT DOCUMENTS

EP    2348964    5/2013

OTHER PUBLICATIONS

T. Wang, C. Cook, B. Derby, "Fabrication of a Glucose Biosensor by Piezoelectric Inkjet Printing", Third International Conference on Sensor Technologies and Applications, 2009.*

(Continued)

*Primary Examiner* — Eric J Messersmith
(74) *Attorney, Agent, or Firm* — Vorys, Sater, Seymour, and Pease LLP

(57) ABSTRACT

Embodiments of the present disclosure relate to analyte determining methods and devices (e.g., electrochemical analyte monitoring systems) that have a sensing surface that includes two or more sensing elements disposed laterally to each other, where the sensing surface is on a working electrode of in vivo and/or in vitro analyte sensors, e.g., continuous and/or automatic in vivo monitoring using analyte sensors and/or test strips. Also provided are systems and methods of using the, for example electrochemical, analyte sensors in analyte monitoring.

37 Claims, 13 Drawing Sheets

(56) References Cited

U.S. PATENT DOCUMENTS

| | | | |
|---|---|---|---|
| 6,134,461 A | 10/2000 | Say et al. | |
| 6,139,718 A * | 10/2000 | Kurnik | C12Q 1/54 |
| | | | 204/403.14 |
| 6,143,164 A | 11/2000 | Heller et al. | |
| 6,175,752 B1 | 1/2001 | Say et al. | |
| 6,262,264 B1 * | 7/2001 | Buck, Jr. | C07F 15/0026 |
| | | | 205/792 |
| 6,338,790 B1 | 1/2002 | Feldman et al. | |
| 6,579,690 B1 | 6/2003 | Bonnecaze et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,616,819 B1 | 9/2003 | Liamos et al. | |
| 6,650,471 B2 | 11/2003 | Doi | |
| 6,654,625 B1 | 11/2003 | Say et al. | |
| 6,736,957 B1 | 5/2004 | Forrow et al. | |
| 6,746,582 B2 | 6/2004 | Heller et al. | |
| 6,893,545 B2 | 5/2005 | Gotoh et al. | |
| 6,932,894 B2 | 8/2005 | Mao et al. | |
| 7,090,756 B2 | 8/2006 | Mao et al. | |
| 7,452,452 B2 * | 11/2008 | Ren | B82Y 10/00 |
| | | | 204/400 |
| 7,501,053 B2 | 3/2009 | Karinka et al. | |
| 7,754,093 B2 | 7/2010 | Forrow et al. | |
| 7,811,231 B2 | 10/2010 | Jin et al. | |
| 2004/0040868 A1 * | 3/2004 | DeNuzzio | B01L 3/5085 |
| | | | 205/792 |
| 2005/0272989 A1 | 12/2005 | Shah et al. | |
| 2006/0004272 A1 | 1/2006 | Shah et al. | |
| 2006/0025662 A1 | 2/2006 | Buse et al. | |
| 2006/0091006 A1 | 5/2006 | Wang et al. | |
| 2006/0211921 A1 * | 9/2006 | Brauker | A61B 5/14532 |
| | | | 600/309 |
| 2007/0068807 A1 | 3/2007 | Feldman et al. | |
| 2007/0095661 A1 | 5/2007 | Wang et al. | |
| 2007/0108048 A1 | 5/2007 | Wang et al. | |
| 2007/0199818 A1 | 8/2007 | Petyt et al. | |
| 2008/0066305 A1 | 3/2008 | Wang et al. | |
| 2008/0102441 A1 | 5/2008 | Chen et al. | |
| 2008/0148873 A1 | 6/2008 | Wang | |
| 2008/0177164 A1 | 7/2008 | Heller et al. | |
| 2008/0179187 A1 | 7/2008 | Ouyang et al. | |
| 2008/0194990 A1 | 8/2008 | Heller et al. | |
| 2008/0214916 A1 | 9/2008 | Yodfat et al. | |
| 2008/0267823 A1 | 10/2008 | Wang et al. | |
| 2008/0288180 A1 * | 11/2008 | Hayter | A61B 5/0008 |
| | | | 702/23 |
| 2009/0084678 A1 * | 4/2009 | Joshi | A61B 5/14532 |
| | | | 204/403.14 |
| 2009/0095625 A1 | 4/2009 | Forrow | |
| 2009/0184000 A1 * | 7/2009 | Brenneman | A61B 5/14507 |
| | | | 205/775 |
| 2009/0198117 A1 * | 8/2009 | Cooper | A61B 5/14532 |
| | | | 600/347 |
| 2009/0255811 A1 | 10/2009 | Forrow et al. | |
| 2009/0294306 A1 * | 12/2009 | Feldman | G01N 27/301 |
| | | | 205/792 |
| 2009/0308742 A1 | 12/2009 | Paranjape | |
| 2010/0094111 A1 | 4/2010 | Heller et al. | |
| 2010/0213057 A1 | 8/2010 | Feldman et al. | |
| 2010/0243478 A1 | 9/2010 | Feldman et al. | |
| 2011/0120865 A1 | 5/2011 | Bommakanti et al. | |
| 2011/0124993 A1 | 5/2011 | Bommakanti et al. | |
| 2011/0124994 A1 | 5/2011 | Bommakanti et al. | |
| 2011/0196216 A1 * | 8/2011 | Quarder | A61B 5/14532 |
| | | | 600/345 |
| 2012/0088993 A1 * | 4/2012 | Buck | A61B 5/1473 |
| | | | 600/345 |

OTHER PUBLICATIONS

International Search Report for PCT/US2011/064000 dated Apr. 5, 2012.

* cited by examiner

ANALYTE SENSORS WITH A SENSING SURFACE HAVING SMALL SENSING SPOTS

CROSS-REFERENCE TO RELATED APPLICATIONS

Pursuant to 35 U.S.C. § 119(e), this application claims priority to U.S. Provisional Patent Application No. 61/421,371 filed on Dec. 9, 2010, the disclosure of which is herein incorporated by reference in its entirety.

INTRODUCTION

In many instances it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis. A number of systems that allow individuals to easily monitor their blood glucose are currently available. Such systems include electrochemical biosensors, including those that comprise a glucose sensor that is adapted for insertion into a subcutaneous site within the body for the continuous monitoring of glucose levels in bodily fluid of the subcutaneous site (see for example, U.S. Pat. No. 6,175,752 to Say et al).

A person may obtain a blood sample by withdrawing blood from a blood source in his or her body, such as a vein, using a needle and syringe, for example, or by lancing a portion of his or her skin, using a lancing device, for example, to make blood available external to the skin, to obtain the necessary sample volume for in vitro testing. The person may then apply the fresh blood sample to a test strip, whereupon suitable detection methods, such as calorimetric, electrochemical, or photometric detection methods, for example, may be used to determine the person's actual blood glucose level. The foregoing procedure provides a blood glucose concentration for a particular or discrete point in time, and thus, must be repeated periodically, in order to monitor blood glucose over a longer period.

In addition to the discrete or periodic, in vitro, blood glucose-monitoring systems described above, at least partially implantable, or in vivo, blood glucose-monitoring systems, which are constructed to provide continuous in vivo measurement of an individual's blood glucose concentration, have been described and developed.

Such analyte monitoring devices are constructed to provide for continuous or automatic monitoring of analytes, such as glucose, in the blood stream or interstitial fluid. Such devices include electrochemical sensors, at least a portion of which are operably positioned in a blood vessel or in the subcutaneous tissue of a user.

While continuous glucose monitoring is desirable, there are several challenges associated with optimizing manufacture protocols to improve yield and uniformity of the sensing elements of the biosensors constructed for in vivo use. Accordingly, further development of manufacturing techniques and methods, as well as analyte-monitoring devices, systems, or kits employing the same, is desirable.

SUMMARY

Embodiments of the present disclosure relate to analyte determining methods and devices (e.g., electrochemical analyte monitoring systems) that have a sensing surface that includes two or more sensing elements disposed laterally to each other, where the sensing surface is on a working electrode of in vivo and/or in vitro analyte sensors, e.g., continuous and/or automatic in vivo monitoring using analyte sensors and/or test strips. Also provided are systems and methods of using the, for example electrochemical, analyte sensors in analyte monitoring.

Aspects of the present disclosure include an analyte sensor that includes: a working electrode; and a counter electrode, where the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 µm to 500 µm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 µm or less.

In certain embodiments, at least a portion of the analyte sensor is adapted to be subcutaneously positioned in a subject.

In some instances, the analyte sensor further includes a membrane disposed over the sensing elements that limits flux of analyte to the sensing elements.

In some cases, the analyte-responsive enzyme includes a glucose-responsive enzyme. In certain instances, the sensing elements include a redox mediator. For example, the redox mediator may include a ruthenium-containing complex or an osmium-containing complex.

In certain embodiments, the analyte sensor is a glucose sensor. In some cases, the analyte sensor is an in vivo sensor. In other cases, the analyte sensor is an in vitro sensor.

Aspects of the present disclosure also include a method for monitoring a level of an analyte in a subject. The method includes positioning at least a portion of an analyte sensor into skin of a subject, and determining a level of an analyte over a period of time from signals generated by the analyte sensor, where the determining over a period of time provides for monitoring the level of the analyte in the subject. As described above, the analyte sensor includes: a working electrode; and a counter electrode, wherein the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 μm or less.

In certain embodiments, at least a portion of the analyte sensor is adapted to be subcutaneously positioned in a subject.

In some instances, the analyte sensor further includes a membrane disposed over the sensing elements that limits flux of analyte to the sensing elements.

In some cases, the analyte-responsive enzyme includes a glucose-responsive enzyme. In certain instances, the sensing elements include a redox mediator. For example, the redox mediator may include a ruthenium-containing complex or an osmium-containing complex.

In certain embodiments, the analyte sensor is a glucose sensor. In some cases, the analyte sensor is an in vivo sensor. In other cases, the analyte sensor is an in vitro sensor.

Aspects of the present disclosure further include a method for monitoring a level of an analyte using an analyte monitoring system. The method includes: inserting at least a portion of an analyte sensor into skin of a patient; attaching an analyte sensor control unit to the skin of the patient; coupling a plurality of conductive contacts of the analyte sensor control unit to a plurality of contact pads of the analyte sensor; collecting data, using the analyte sensor control unit, regarding a level of an analyte from signals generated by the analyte sensor; and transmitting the collected data from the analyte sensor control unit to a receiver unit. As described above, the analyte sensor includes a working electrode and a counter electrode, where the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 μm or less.

In certain embodiments, the analyte is glucose.

In some instances, the collecting data includes generating signals from the analyte sensor and processing the signals into data. In certain cases, the data comprise the signals from the analyte sensor.

In certain embodiments, the method further includes activating an alarm if the data indicate an alarm condition. In some cases, the method further includes administering a drug in response to the data. For example, the drug may be insulin.

In certain instances, the method does not include a calibration step.

Aspects of the present disclosure also include a method of fabricating an electrode for use in an analyte sensor. The method includes contacting a sensing surface of a working electrode with two or more sensing elements disposed laterally to each other, where each sensing element comprises an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 μm or less.

In certain embodiments, the method is a method of fabricating two or more electrodes for use in a plurality of analyte sensors. In these embodiments, the method includes contacting a sensing surface on each of the two or more electrodes with two or more sensing elements disposed laterally to each other, wherein each sensing element comprises an analyte-responsive enzyme. In some instances, the electrodes have a coefficient of variation in sensitivity of 8% or less.

In certain cases, at least a portion of the analyte sensor is adapted to be subcutaneously positioned in a subject. In some instances, the analyte sensor further includes a membrane disposed over the sensing elements.

In certain embodiments, the analyte-responsive enzyme includes a glucose-responsive enzyme. In some cases, the sensing elements include a redox mediator. For example, the redox mediator may include a ruthenium-containing complex or an osmium-containing complex.

In certain instances, the analyte sensor is a glucose sensor. In some cases, the analyte sensor is an in vivo sensor. In other instances, the analyte sensor is an in vitro sensor.

In certain embodiments of the method, the contacting includes depositing one or more drops comprising the sensing elements onto the sensing surface of the working electrode. In some cases, the method further includes contacting the sensing elements with a membrane that limits flux of analyte to the sensing elements.

Aspects of the present disclosure also include an analyte test strip that includes: a first substrate having a first surface; a second substrate having a second surface opposing the first surface, the first and second substrates being disposed so that the first surface is in facing relationship with the second surface; a working electrode disposed on the first surface; and a counter electrode disposed on one of the first surface and the second surface, where the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 μm or less.

In certain embodiments, the analyte test strip further includes a spacer between the first substrate and the second substrate.

In some cases, the analyte-responsive enzyme includes a glucose-responsive enzyme. In certain instances, the sensing elements includes a redox mediator. For example, the redox mediator may include a ruthenium-containing complex or an osmium-containing complex.

In certain embodiments, the analyte test strip is a glucose test strip.

Aspects of the present disclosure further include a method for monitoring a level of an analyte in a subject. The method includes contacting a sample from a subject to an analyte test strip and determining a level of an analyte from a signal generated by the analyte test strip, where the determining provides for monitoring the level of the analyte in the subject. As described above, the analyte test strip includes: a first substrate having a first surface; a second substrate having a second surface opposing the first surface, the first and second substrates being disposed so that the first surface is in facing relationship with the second surface; a working electrode disposed on the first surface; and a counter electrode disposed on one of the first surface and the second surface, where the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 μm or less.

In certain embodiments, the method further includes a spacer between the first substrate and the second substrate.

In some cases, the analyte-responsive enzyme includes a glucose-responsive enzyme. In certain instances, the sensing elements include a redox mediator. For example, the redox mediator may include a ruthenium-containing complex or an osmium-containing complex.

In certain embodiments, the analyte test strip is a glucose test strip.

Aspects of the present disclosure also include a method for monitoring a level of an analyte using an analyte monitoring system. The method includes: coupling a conductive contact of an analyte test strip to an analyte monitoring system; contacting a sample from a subject to the analyte test strip; collecting data, using the analyte monitoring system, regarding a level of an analyte from a signal generated by the analyte test strip; and determining a level of an analyte from the collected data, where the determining provides for monitoring the level of the analyte in the subject. As discussed above, the analyte test strip includes: a first substrate having a first surface; a second substrate having a second surface opposing the first surface, the first and second substrates being disposed so that the first surface is in facing relationship with the second surface; a working electrode disposed on the first surface; and a counter electrode disposed on one of the first surface and the second surface, where the working electrode includes a sensing surface having two or more sensing elements disposed laterally to each other, where each sensing element includes an analyte-responsive enzyme.

In certain embodiments, the sensing elements are discontiguous. In some cases, the sensing elements are arranged as individual sensing elements on the working electrode. For example, the sensing surface may include an array of two or more individual sensing elements. In some cases, the sensing surface includes an array of 100 or more individual sensing elements. In certain instances, the sensing surface has a density of sensing elements ranging from 2-1000 sensing elements/mm$^2$.

In certain embodiments, the sensing surface further includes inter-feature areas. The inter-feature areas may surround the sensing elements. In some instances, the sensing elements have an inter-feature distance ranging from 1 μm to 500 μm. In certain cases, the inter-feature areas are free of the analyte-responsive enzyme. In some cases, the inter-feature areas are free of a redox mediator.

In certain embodiments, the working electrode further includes a second layer of two or more sensing elements disposed on the sensing surface. In some instances, the sensing elements have an average diameter of 200 µm or less.

In certain embodiments, the analyte is glucose.

In some instances of the method, the collecting data includes generating the signal from the analyte test strip and processing the signal into data. In certain cases, the data include the signals from the analyte test strip.

In certain instances, the method further includes activating an alarm if the data indicate an alarm condition. In some cases, the method further includes administering a drug in response to the data. For example, the drug may be insulin.

In certain embodiments, the method does not include a calibration step.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
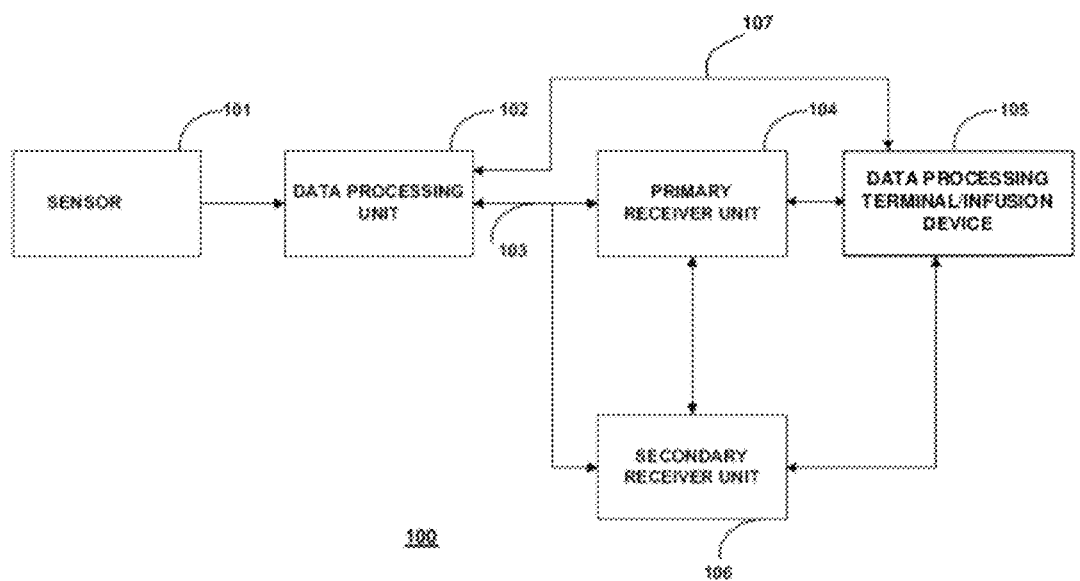
FIG. 1 shows a block diagram of an embodiment of an analyte monitoring system according to embodiments of the present disclosure.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

Systems and Methods Having Two or More Sensing Elements

Embodiments of the present disclosure relate to methods and devices for reducing variation in sensor sensitivity by including a sensing surface that includes two or more sensing elements disposed laterally to each other, where the sensing surface is on a working electrode of the sensor, such as in vivo and/or in vitro analyte sensors, including continuous and/or automatic in vivo analyte sensors. For example, embodiments of the present disclosure provide for a sensing surface of a working electrode that includes an array of two or more individual sensing elements, resulting in a decrease in variation of the sensor sensitivity between individual sensors. Also provided are systems and methods of using the analyte sensors in analyte monitoring.

Embodiments of the present disclosure are based on the discovery that deposition of two or more sensing elements disposed laterally to each other on a sensing surface of a working electrode in the manufacture of in vivo and/or in vitro biosensors reduces variation in sensor sensitivity between sensors. In certain embodiments, a sensor that includes two or more sensing elements disposed laterally to each other on a sensing surface of a working electrode has a variation in sensor sensitivity that is lower than a sensor with one single larger sensing element. Stated another way, sensors may have a lower variation in sensor sensitivity for a sensor that includes two or more sensing elements disposed laterally to each other on a sensing surface of a working electrode such that the total sensing element area per sensor is less than a sensor that has a single larger sensing element with a greater total sensing element area per sensor. In certain embodiments, sensors that include two or more sensing elements disposed laterally to each other on a sensing surface of a working electrode have a coefficient of variation in sensitivity of 20% or less, such as 15% or less, including 10% or less, such as 8% or less, or 5% or less, or 3% or less, or 2% or less, or 1% or less.

During the manufacturing process for the subject analyte sensors, an aqueous solution (e.g., a sensing element formulation) is contacted with a surface of a substrate (e.g., a surface of a working electrode), forming a deposition of the solution (e.g., a sensing element) on the surface of the substrate. The sensing elements may include an analyte-responsive enzyme. In certain instances, the sensing elements include a redox mediator. In some cases, the sensing element formulation is deposited such that the sensing elements are discontiguous. By "discontiguous" is meant that a sensing element does not share an edge or boundary (e.g., is not touching) an adjacent sensing element. For example, the sensing elements may be arranged as individual (e.g., discreet) sensing elements on the surface of the working electrode. In other embodiments, the sensing elements are deposited on the surface of the working electrode such that the edges of the sensing elements contact the edges of one or more adjacent sensing elements. In these embodiments, the sensing elements may be referred to as "contiguous".

In certain embodiments, the sensing surface includes an array of two or more individual sensing elements on the working electrode. As used herein, the term "array" refers to any one-dimensional, two-dimensional or substantially two-dimensional (as well as a three-dimensional) arrangement of regions bearing a particular composition associated with that region. In some instances, the arrays are arrays of a formulation, such as a sensing element formulation. As such, in some embodiments, the arrays are arrays of individual sensing elements, where each sensing element includes a sensing element formulation.

Any given substrate may carry one, two, four or more arrays of sensing elements disposed on a surface of the substrate. Depending upon the use, any or all of the arrays may be the same or different from one another and each may contain multiple spots or features (e.g., sensing elements). For example, an array may include two or more, 5 or more, ten or more, 25 or more, 50 or more, 100 or more features, or even 1000 or more features, in an area of 100 $mm^2$ or less, such as 75 $mm^2$ or less, or 50 $mm^2$ or less, for instance 25 $mm^2$ or less, or 10 $mm^2$ or less, or 5 $mm^2$ or less, such as 2 $mm^2$ or less, or 1 $mm^2$ or less, 0.5 $mm^2$ or less, or 0.1 $mm^2$ or less. For example, features may have widths (that is, diameter, for a round spot) in the range from 0.1 µm to 1 mm, or from 1 µm to 1 mm, such as ranging from 1 µm to 500 µm, including from 10 µm to 250 µm, for example from 50 µm to 200 µm. In certain embodiments, the sensing elements have an average diameter of 500 µm or less, such as 250 µm or less, including 200 µm or less, or 150 µm or less, or 100 µm or less, such as 50 µm or less, or 10 µm or less, or 1 µm or less, or 0.1 µm or less. Non-round features may have area ranges equivalent to that of circular features with the foregoing width (diameter) ranges.

In certain embodiments, the sensing surface includes inter-feature areas. Inter-feature areas do not carry any sensing element formulation. As such, in some instances, the inter-feature areas do not include (e.g., are substantially free of) an analyte-responsive enzyme. In addition, in some cases, the inter-feature areas do not include (e.g., are substantially free of) a redox mediator or polymer bound, covalently or non-covalently, redox mediator. The inter-feature areas may substantially surround the sensing elements, such that, as described herein, the sensing elements are discontiguous. In some cases, the sensing elements have inter-feature areas, wherein the distance between adjacent sensing elements (e.g., the inter-feature distance) is such that the flux of analyte to a sensing element does not significantly interfere with the flux of analyte to adjacent sensing elements. For example, the inter-feature distance may be 0.1 µm or more, 0.5 µm or more, 1 µm or more, such as 10 µm or more, including 50 µm or more, or 100 µm or more, or 150 µm or more, or 200 µm or more, or 250 µm or more, for instance 500 µm or more. The inter-feature distance may range from 0.1 µm to 500 µm, or from 0.5 µm to 500 µm, or from 1 µm to 500 µm, such as from 1 µm to 250 µm, including from 5 µm to 200 µm, for instance from 10 µm to 200 µm. Such inter-feature areas may be present where the arrays are formed by processes involving drop deposition of the sensing element formulation onto a sensing surface of a working electrode, as described in more detail below. It will be appreciated that the inter-feature areas, when present, could be of various sizes and configurations.

Each array may cover an area of 100 mm$^2$ or less, or 50 mm$^2$, or 25 mm$^2$ or less, such as 10 mm$^2$, 5 mm$^2$ or less, 1 mm$^2$ or less, or 0.1 mm$^2$ or less, or 0.01 mm$^2$ or less, for instance 0.001 mm$^2$ or less. In some embodiments, the sensing surface has a density of sensing elements of 2 sensing elements/mm$^2$ or more, such as 5 sensing elements/mm$^2$ or more, including 10 sensing elements/mm$^2$ or more, or 50 sensing elements/mm$^2$ or more, or 100 sensing elements/mm$^2$ or more, such as 250 sensing elements/mm$^2$ or more, including 500 sensing elements/mm$^2$ or more, or 1000 sensing elements/mm$^2$ or more. For example, the sensing surface may have a density of sensing elements ranging from 2-1000 sensing elements/mm$^2$, such as 2-500 sensing elements/mm$^2$, including 2-250 sensing elements/mm$^2$, or 2-100 sensing elements/mm$^2$, or 2-50 sensing elements/mm$^2$, such as 2-10 sensing elements/mm$^2$.

Arrays can be fabricated using drop deposition of the sensing element formulation onto a sensing surface of a working electrode. For example, the sensing element formulation may be deposited by any non-impact or impact printing method, such as, for example, from a pulse-jet device. A "pulse-jet" is a device that can dispense drops in the formation of an array. Pulse-jet devices operate by delivering a pulse of pressure to liquid adjacent an outlet or orifice such that a drop will be dispensed therefrom (for example, by a piezoelectric or thermoelectric element positioned in the same chamber as the orifice). In certain embodiments, the drops may be dispensed using a dispenser device configured to operate similar to an inkjet printing device, as described above. In certain embodiments, the pulse-jet device includes a dispensing head configured to dispense drops, such as, but not limited to, sensing layer formulation, in the formation of an array. The dispensing head may be of a type commonly used in an inkjet type of printer and may, for example, include one or more deposition chambers for containing the formulation(s) to be deposited. The amount of fluid that is deposited in a single activation event of a pulse jet can be controlled by changing one or more of a number of parameters, including the size of the orifice in the dispensing head (e.g., the orifice diameter), the size of the deposition chamber, the size of the piezoelectric or thermoelectric element, etc. The amount of fluid deposited during a single activation event may range from 0.01 to 1000 picoliters (pL), such as from 0.1 to 750 pL, including from 1 to 500 pL, or form 1 to 250 pL, or from 1 to 100 pL, for instance from 1 to 75 pL, or from 1 to 50 pL, such as from 1 to 25 pL, or from 1 to 10 pL, for example from 1 to 5 pL. In certain cases, the amount of fluid deposited during a single activation event may range from 1 to 50 pL.

In certain embodiments, during the manufacturing process for the subject analyte sensors, an aqueous solution (e.g., a sensing layer formulation) is contacted with a surface of a substrate (e.g., a surface of a working electrode), forming a deposition of the solution on the surface of the substrate. In some cases, the solution is allowed to dry and cure. Without being limited to any particular theory, in certain instances, during the drying, the constituents of the solution may tend to migrate towards the outer edges of the deposition due to a faster rate of evaporation at the thinner peripheral edges of the deposition. This results in a greater concentration of the constituents of the solution at the peripheral edges of the deposition, resulting in a so-called "coffee ring" effect. Analyte sensors are typically manufactured by depositing a stripe or relatively large drop of a sensing layer formulation onto the surface of an electrode, which, in some cases, may result in a "coffee ring" effect as described above. For example, as described above, when an elongated stripe of sensing layer formulation dries on the surface of the electrode, constituents in the sensing layer formulation may migrate towards the outer edges of the stripe, resulting in an uneven coating of the sensing layer formulation on the surface of the electrode with a higher concentration of the sensing layer formulation near the edges of the sensing layer stripe.

In certain embodiments of the present disclosure, the deposition of an array of small sensing elements may result in a reduction, and in some cases, complete elimination of the "coffee ring" effect. For instance, the coffee-ring effect may be minimized by depositing an array of two or more individual sensing elements on the working electrode. In some cases, due to their small size, the small sensing elements in the array have a rate of evaporation that is greater than the rate of evaporation of a sensing layer formulation deposited as a stripe or a relatively large drop on the surface of the electrode. In certain embodiments, the faster rate of evaporation results in a more uniform distribution of the constituents of the solution deposited on the substrate upon drying and curing as compared to a solution deposited as a relatively larger stripe or drop of the sensing layer formulation. This, in turn, may improve the coefficient of variation and the overall manufacturing process of the sensor and overall system. In certain embodiments, small sensing elements may facilitate faster sensor fabrication due to faster drying of the very small sensing element spots, even at room temperature. Drying time may further be decreased by drying the sensing elements above room temperature, such as at a temperature of 25-100° C., such as 30-80° C., including 40-60° C.

In some instances, each sensing element (e.g., feature on the array) has a volume ranging from 0.01 to 1000 picoliters (pL), such as from 0.1 to 750 pL, including from 1 to 500 pL, or form 1 to 250 pL, or from 1 to 100 pL, for instance from 1 to 75 pL, or from 1 to 50 pL, such as from 1 to 25 pL, or from 1 to 10 pL, for example from 1 to 5 pL. In certain cases, each sensing element has a volume ranging from 1 to 50 pL. As described above, the array of sensing elements may be deposited on the surface of the electrode such that there is an inter-feature area between each individual sensing element on the array, such that the sensing elements are discontiguous.

In certain embodiments, a single layer of sensing elements is deposited on the surface of the working electrode. In other cases, two or more layers of sensing elements are deposited on the surface of the working electrode. For example, the working electrode may include a sensing surface that includes a first layer of sensing elements as described above, and may further include a second layer of sensing elements disposed on the sensing surface. In these cases, the first layer may be deposited as a first array of sensing elements on the surface of the working electrode. A second layer of sensing elements may be deposited as a second array of sensing elements disposed on the first array of sensing elements. In some cases, the second array of sensing elements is deposited such that each sensing element in the second array is substantially aligned on top of a corresponding sensing element of the first array of sensing elements. In other instances, the second array of sensing elements is deposited such that each sensing element in the second array is deposited substantially on top of an inter-feature area of the first array of sensing elements. In these instances, the second array of sensing elements may be offset from the positions of the sensing elements in the first array of sensing elements. In some instances, the second layer of sensing elements may overlap at least a portion of one or more sensing elements in the underlying first layer of sensing elements. The deposition of a first array and second array of sensing elements in an offset configuration as described above may facilitate the formation of a contiguous coating of the sensing layer formulation on the surface of the working electrode. Additional layers of sensing elements may be deposited on the working electrode, either substantially aligned with the underlying layer or offset from the underlying layer, as desired. The deposition of multiple layers of sensing elements on the surface of the working electrode may facilitate the cumulative deposition of a desired total quantity of the sensing layer formulation on the surface of the working electrode.

Figure 10:
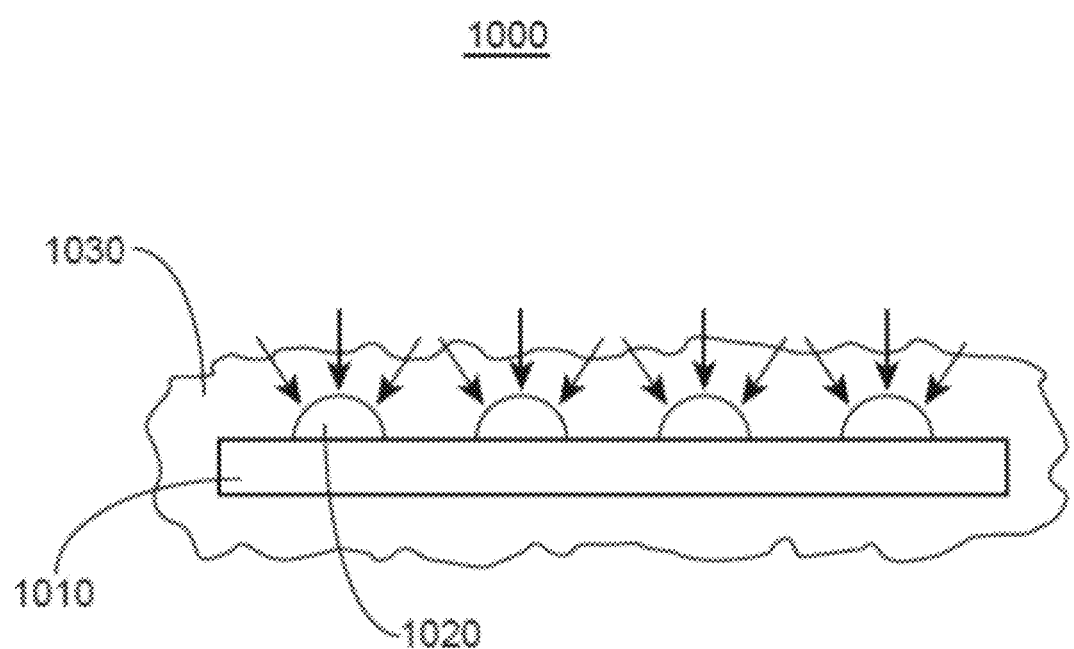
FIG. 10 shows a cross-sectional view of a working electrode that has a plurality of sensing elements on the surface of a working electrode according to embodiments of the present disclosure.

Without being limited to any particular theory, in certain instances, the sensitivity of an analyte sensor depends on the area of the sensing layer, e.g., a layer disposed on a surface of a working electrode that includes a sensing formulation having an analyte-responsive enzyme, and in some cases a redox mediator or a redox mediator bound, covalently or non-covalently, to a polymer. For sensing layers that are a contiguous layer of the sensing layer formulation, the sensor sensitivity depends on the area of the sensing layer and does not significantly depend on edge effects of the sensing layer. For instance, the sensitivity of the sensor may depend on the flux of analyte through a flux limiting membrane disposed over the sensing layer in a 2-dimensional manner towards a surface of the working electrode (e.g., towards a planar surface). In certain embodiments, inclusion of two or more sensing elements disposed laterally to each other allows the area of the sensing elements to be minimized, such that edge effects of the sensing layer are maximized. This may result in the sensor sensitivity being dependent on edge effects of the sensing elements, rather than the overall area of the sensing elements. As such, the sensitivity of the sensor may depend on the flux of analyte through a flux limiting membrane disposed over the sensing elements in a radial 3-dimensional manner towards the working electrode (e.g., towards a point). In certain cases, the sensing elements have an arcuate profile to promote radial diffusion of the analyte through the flux limiting membrane disposed over the sensing elements towards the working electrode. For example, FIG. 10 shows a cross-sectional view of a working electrode 1000 that has a plurality of sensing elements 1020 on the surface of a working electrode 1010. The sensing elements 1020 have an arcuate cross-sectional profile configured to promote radial diffusion (as shown by the arrows) of the analyte through the flux limiting membrane 1030 disposed over the sensing elements 1020 towards the working electrode 1010.

In some instances, the sensing elements have an arcuate profile. By "arcuate" is meant that the cross-sectional profile of the sensing elements have an arc or rounded shape. In certain cases, the sensing elements have a shape approximating that of a half sphere, where the rounded semi-spherical portion of the sensing element is convex and extends a distance above the surface of the substrate (e.g., the surface of the working electrode). In some instances, semi-spherical sensing elements may have a surface area that is greater that the surface area of a typical substantially flat or non-semi-spherically shaped sensing element. For example, semi-spherical sensing elements may have a surface area that is 1.1 or more times greater than the surface area of a typical substantially flat (e.g., non-semi-spherically shaped) sensing element, such as 1.2 or more, including 1.3 or more, or 1.4 or more, or 1.5 or more, or 1.6 or more, or 1.7 or more, 1.8 or more, or 1.9 or more, or 2 or more times greater than the surface area of a typical substantially flat (e.g., non-semi-spherically shaped) sensing element. In certain embodiments, sensing elements that have a greater surface area may facilitate an increase in the surface area of the sensing layer formulation that is able to contact the analyte as the analyte diffuses through the flux limiting membrane towards the sensing elements.

In some instances, because the sensor sensitivity depends on edge effects, rather than the overall area of the sensing elements, small relative changes in the area of the sensing elements will not significantly affect the sensitivity of the sensor. In certain embodiments, this results in a decrease in variation of the sensor sensitivity. A decrease in variation of the sensor sensitivity may facilitate calibration of the sensor during the manufacturing process. For example, embodiments of sensors of the present disclosure may be calibrated during the manufacturing process, such that calibration of the sensors by a user is not required. As such, in some cases, systems using sensors of the present disclosure do not need to perform a calibration step prior to use of the sensors by the user for analyte detection.

Figure 5A:
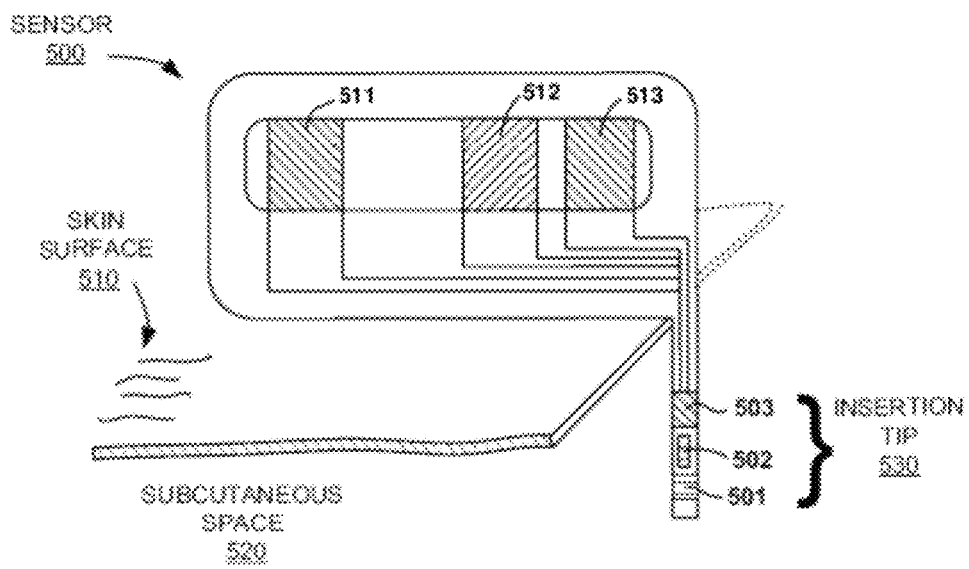
FIGS. 5A-5B show a perspective view and a cross sectional view, respectively, of an embodiment an analyte sensor.
Figure 5B:
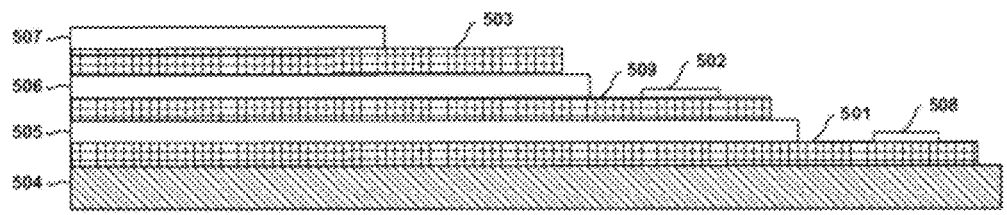
Figure 5C:
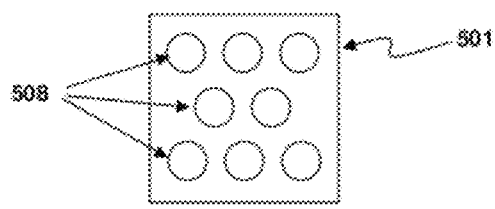
FIG. 5C shows a schematic view of a working electrode according to embodiments of the present disclosure.

An embodiment of a sensing element may be described as the area shown schematically in FIG. 5B as 508. The sensing element may be described as the active chemical area of the biosensor. The sensing element formulation, which can include a glucose-transducing agent, may include, for example, among other constituents, a redox mediator, such as, for example, a hydrogen peroxide or a transition metal complex, such as a ruthenium-containing complex or an osmium-containing complex, and an analyte-responsive enzyme, such as, for example, a glucose-responsive enzyme (e.g., glucose oxidase, glucose dehydrogenase, etc.) or lactate-responsive enzyme (e.g., lactate oxidase). The sensing element may also include other optional components, such as, for example, a polymer and a bi-functional, short-chain, epoxide cross-linker, such as polyethylene glycol (PEG). As described herein, two or more sensing elements may be provided on a sensing surface of the working electrode, where the two or more sensing elements are disposed laterally to each other. For example, FIG. 5C shows a schematic view of a portion of working electrode 501. Working electrode 501 includes a plurality of individual sensing elements 508. The sensing elements 508 are discontiguous, such that the sensing elements 508 are arranged into an array of individual sensing elements 508 on the working electrode 501.

Figure 7A:
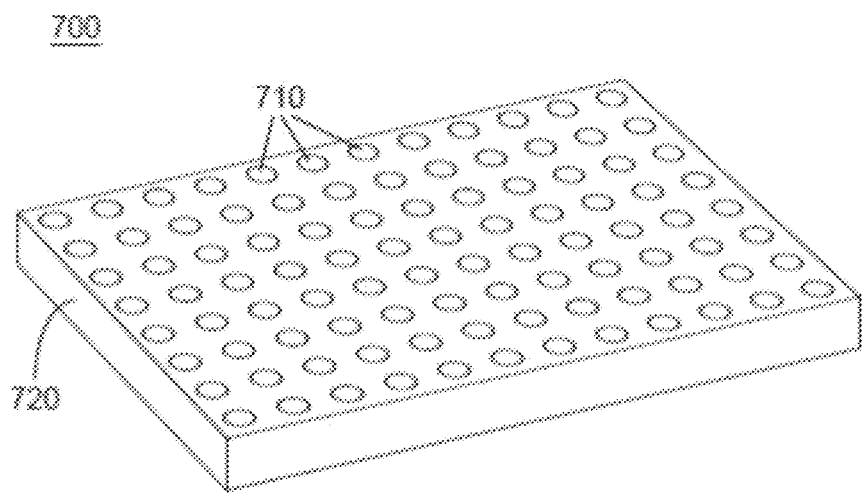
FIG. 7A shows a perspective view of an embodiment of an analyte sensor that has an array of sensing elements in substantially aligned rows according to embodiments of the present disclosure.
Figure 7B:
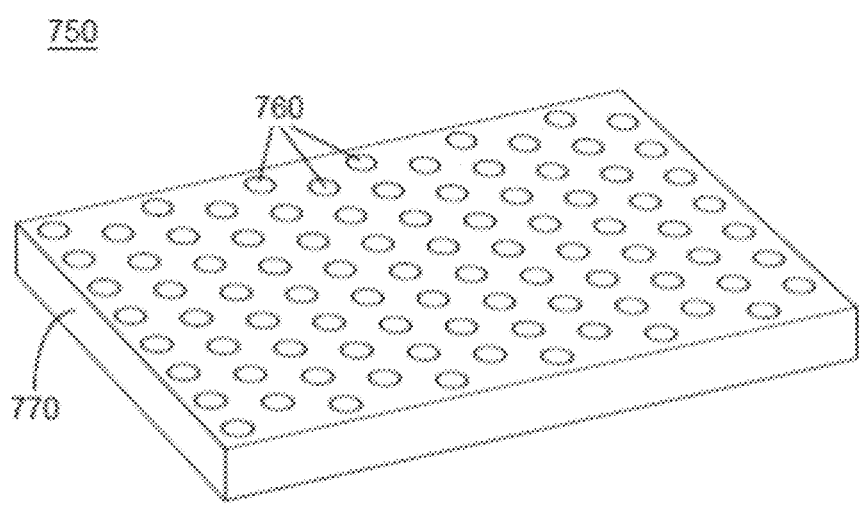
FIG. 7B shows a perspective view of another embodiment of an analyte sensor that has an array of sensing elements in offset rows according to embodiments of the present disclosure.

FIG. 7A shows a schematic view of a portion of an analyte sensor 700 that includes an array of sensing elements 710 deposited on a portion of a working electrode 720. The array of sensing elements 710 is arranged such that each row of sensing elements in the array is substantially aligned with the sensing elements in an adjacent row. As shown in FIG. 7A, the sensing elements 710 are arranged into an array of individual discontiguous sensing elements on the working electrode 720. FIG. 7B shows a schematic view of another embodiment of an analyte sensor 750. The portion of the analyte sensor 750 shown includes an array of sensing element 760 deposited on a portion of a working electrode 770. The array of sensing elements 760 is arranged such that each row of sensing elements in the array is offset from the sensing elements in an adjacent row. As shown in FIG. 7B, the sensing elements 760 are arranged into an array of individual discontiguous sensing elements on the working electrode 770. In some instances, arranging the rows of sensing elements in an offset configuration may facilitate the fabrication of an array with a greater density of sensing elements per unit area as compared to an array with rows of sensing elements substantially aligned, while still maintaining an array of individual discontiguous sensing elements.

Figure 8:
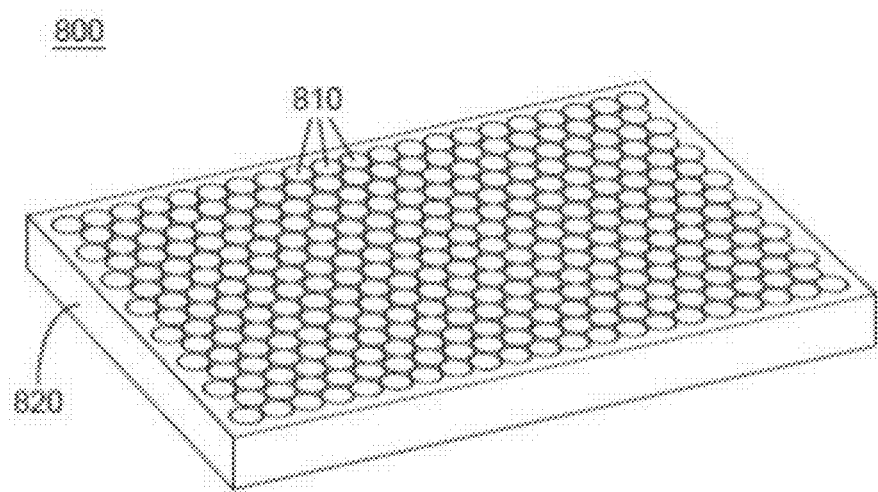
FIG. 8 shows a perspective view of an embodiment of an analyte sensor that has an array of sensing elements in offset rows with minimal inter-feature areas according to embodiments of the present disclosure.

As described above, in other embodiments, the array of sensing elements may be configured such that the inter-feature areas are minimized. For example, FIG. 8 shows an embodiment of an analyte sensor 800 that includes an array of sensing elements 810 disposed on a portion of a working electrode 820. The array of sensing elements 810 is arranged such that each row of sensing elements in the array is offset from the sensing elements in an adjacent row. As shown in FIG. 8, the sensing elements 810 are arranged such that the edges of the sensing elements are in contact with one or more adjacent sensing elements. In some instances, arranging the rows of sensing elements in an offset configuration with the sensing elements in contact with one or more adjacent sensing elements may facilitate the fabrication of an array with a greater density of sensing elements per unit area as compared to an array with discontiguous sensing elements.

Figure 9:
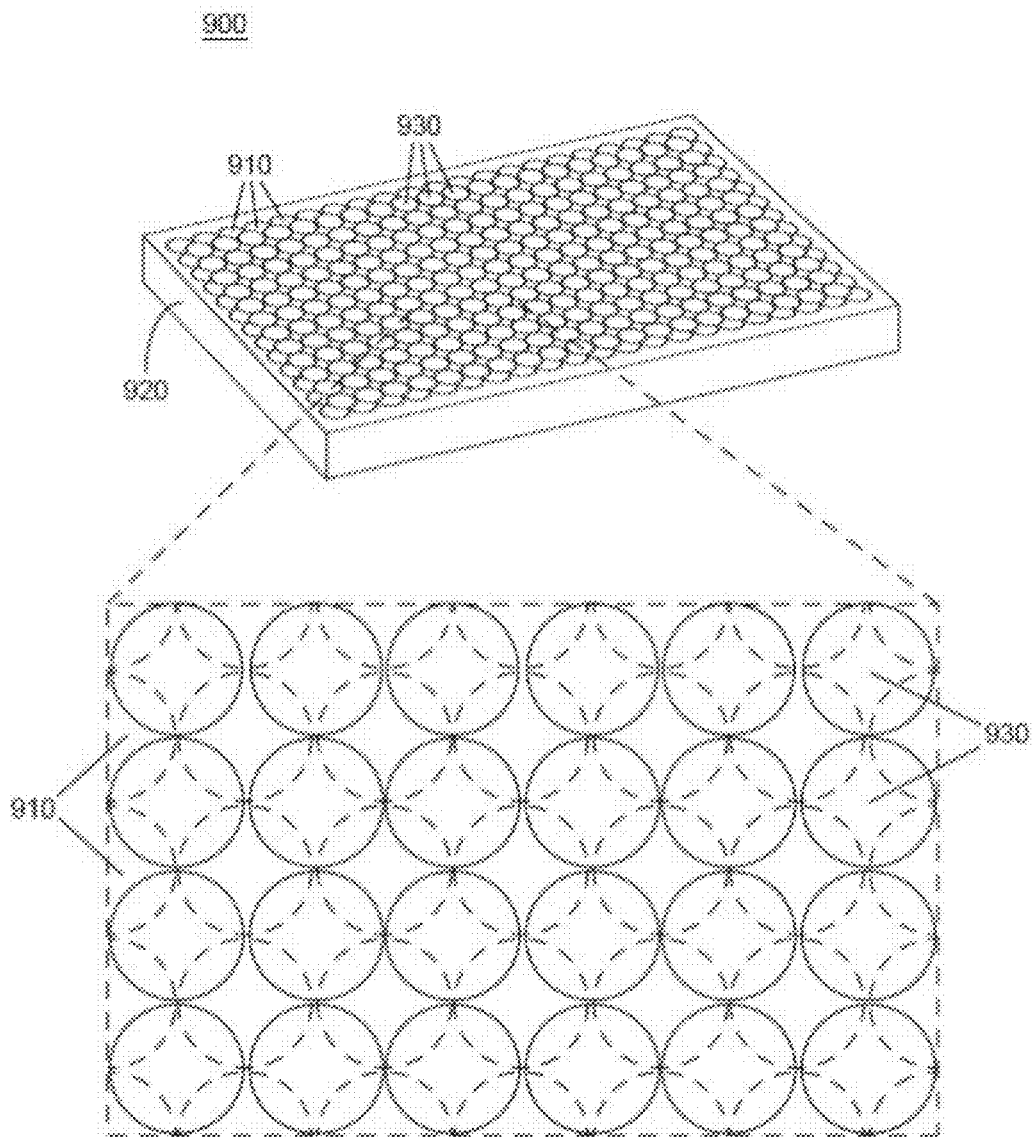
FIG. 9 shows a perspective view of an embodiment of an analyte sensor that has layered arrays of sensing elements according to embodiments of the present disclosure.

As described above, in certain embodiments, two or more layers of sensing elements may be deposited on the surface of a working electrode. For example, FIG. 9 shows a schematic of an analyte sensor 900 that includes sensing elements 910 and 930. Sensing elements 910 of a first layer are deposited as a first array on the surface of a working electrode 920. Sensing elements 930 of a second layer are deposited as a second array disposed on the sensing elements 910 of the first array. As shown in FIG. 9, the sensing elements 930 of the second array are deposited such that each sensing element 930 in the second array is deposited substantially on top of an inter-feature area of the sensing elements 910 of the first array. The sensing elements 930 of the second array are offset from the positions of the sensing elements 910 in the first array. The sensing elements 930 of the second array overlap at least a portion of one or more sensing elements 910 in the underlying first array (see expanded inset in FIG. 9). The deposition of sensing elements 910 in a first array and sensing elements 930 in a second array in an offset configuration as described above may facilitate the formation of a contiguous coating of the sensing layer formulation on the surface of the working electrode 920. Additional layers of sensing elements may be deposited on the working electrode, either substantially aligned with the underlying layer or offset from the underlying layer, as desired.

In an electrochemical embodiment, the sensor is placed, transcutaneously, for example, into a subcutaneous site such that subcutaneous fluid of the site comes into contact with the sensor. In other in vivo embodiments, placement of at least a portion of the sensor may be in a blood vessel. The sensor operates to electrolyze an analyte of interest in the subcutaneous fluid such that a current is generated between the working electrode and the counter electrode. A value for the current associated with the working electrode is determined. If multiple working electrodes are used, current values from each of the working electrodes may be determined. A microprocessor may be used to collect these periodically determined current values or to further process these values.

If an analyte concentration is successfully determined, it may be displayed, stored, transmitted, and/or otherwise processed to provide useful information. By way of example, raw signal or analyte concentrations may be used as a basis for determining a rate of change in analyte concentration, which should not change at a rate greater than a predetermined threshold amount. If the rate of change of analyte concentration exceeds the predefined threshold, an indication maybe displayed or otherwise transmitted to indicate this fact.

As demonstrated herein, the methods of the present disclosure are useful in connection with a device that is used to measure or monitor a glucose analyte, such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof. In general, the device is in good contact, such as thorough and substantially continuous contact, with the bodily fluid.

According to embodiments of the present disclosure, the measurement sensor is one suited for electrochemical measurement of analyte concentration, for example glucose concentration, in a bodily fluid. In these embodiments, the measurement sensor includes at least a working electrode and a counter electrode. Other embodiments may further include a reference electrode. The working electrode may be associated with a glucose-responsive enzyme. A mediator may also be included. In certain embodiments, hydrogen peroxide, which may be characterized as a mediator, is produced by a reaction of the sensor and may be used to infer the concentration of glucose. In some embodiments, a mediator is added to the sensor by a manufacturer, e.g., is included with the sensor prior to use. The redox mediator may be disposed relative to the working electrode and is capable of transferring electrons between a compound and a working electrode, either directly or indirectly. The redox mediator may be, for example, immobilized on the working electrode, e.g., entrapped on a surface or chemically bound to a surface.

Additional embodiments of a sensor that may include a working electrode with a sensing surface that includes two or more sensing elements disposed laterally to each other are described in U.S. Pat. Nos. 5,262,035, 5,262,305, 6,134,461, 6,143,164, 6,175,752, 6,338,790, 6,579,690, 6,605,200, 6,605,201, 6,654,625, 6,736,957, 6,746,582, 6,932,894, 7,090,756 as well as those described in U.S. patent application Ser. Nos. 11/701,138, 11/948,915, 12/625,185, 12/625,208, and 12/624,767, the disclosures of all of which are incorporated herein by reference in their entirety. Moreover, the embodiments disclosed herein may be incorporated into battery-powered or self-powered analyte sensors, such as self-powered analyte sensors, as disclosed in U.S. patent application Ser. No. 12/393,921 (U.S. Patent Application Publication No. 2010/0213057), the disclosure of which is incorporated by reference herein in its entirety. In addition, the embodiments disclosed herein may be incorporated into analyte monitoring systems and devices that utilize one or more rivets to attach an analyte sensor having one or more conductive traces to a sensor control unit, such as disclosed in U.S. Provisional Patent Application No. 61/498,142, filed Jun. 17, 2011, the disclosure of which is incorporated by reference herein in its entirety.

Figure 11:
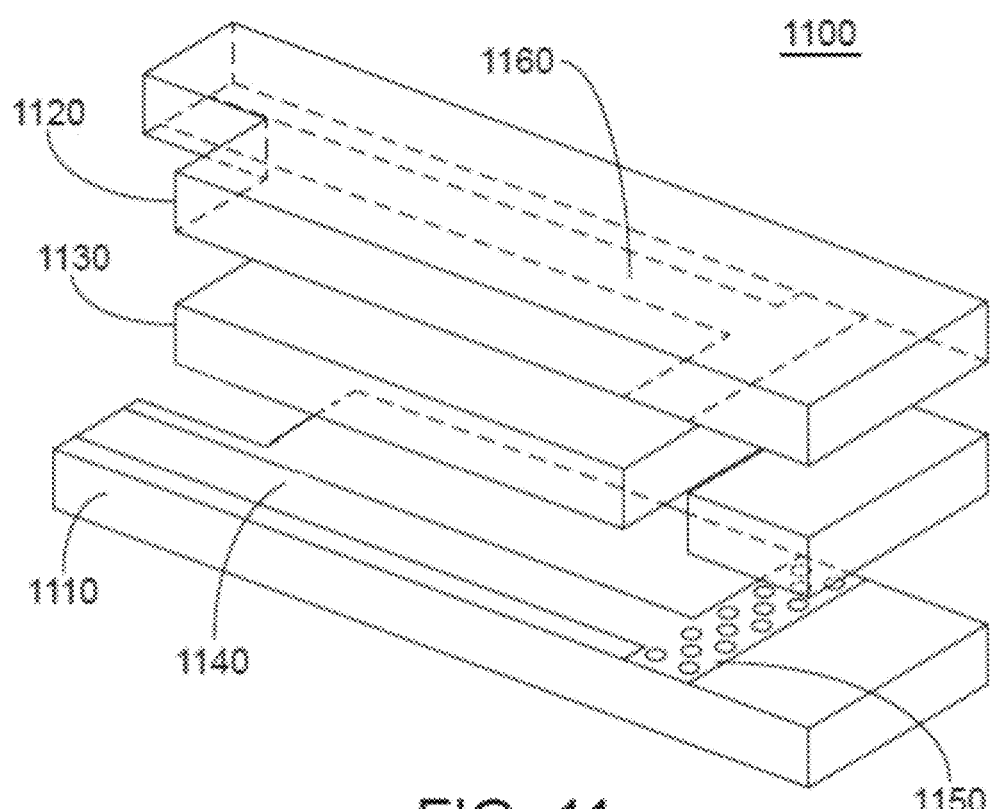
FIG. 11 shows an exploded perspective view of an analyte sensor test strip, the layers illustrated individually with the electrodes in a first configuration according to embodiments of the present disclosure.
Figure 12:
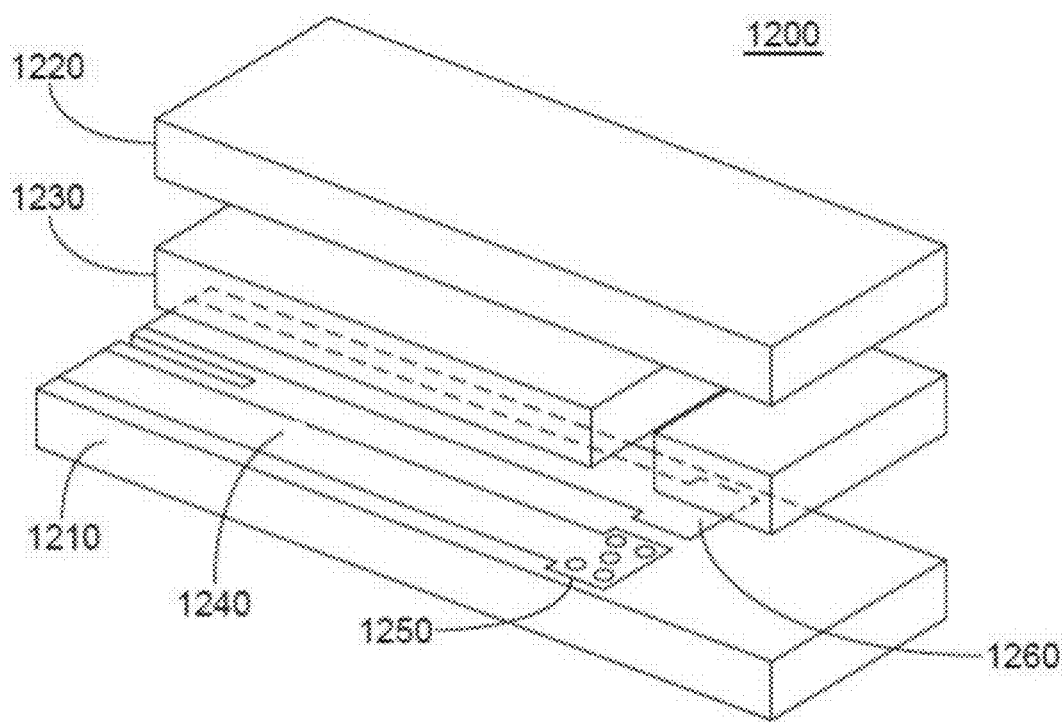
FIG. 12 shows an exploded perspective view of an analyte sensor test strip, the layers illustrated individually with the electrodes in a second configuration according to embodiments of the present disclosure.
Figure 13:
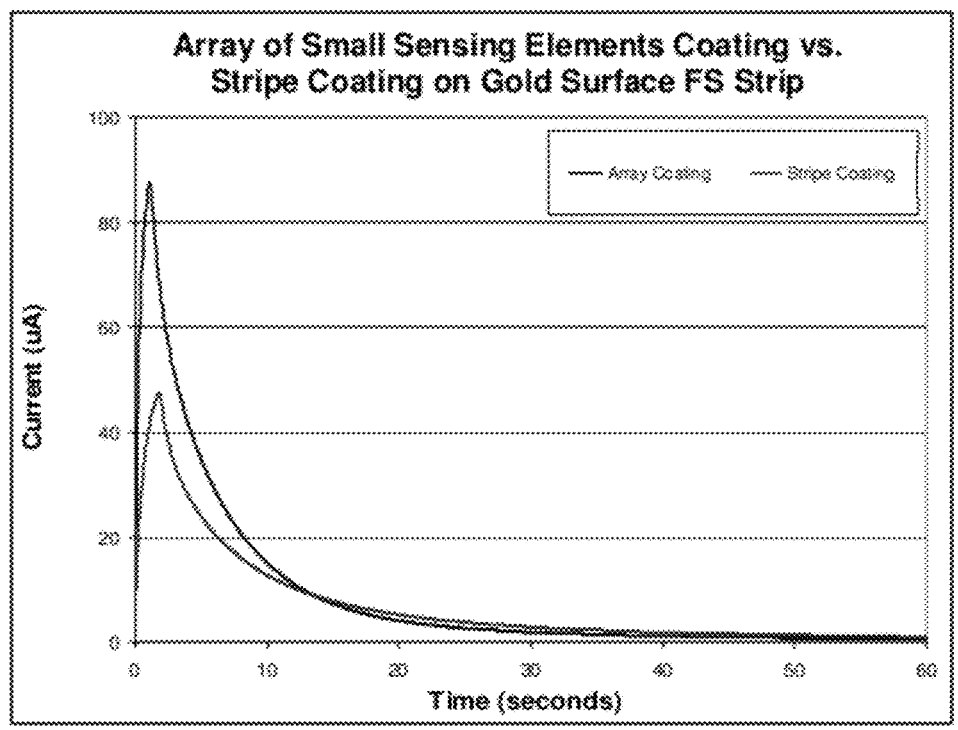
FIG. 13 shows a graph of current (µA) vs. time (seconds) for a sensing layer formulation deposited as an array of small sensing elements vs. a stripe coating according to embodiments of the present disclosure.

Aspects of the present disclosure also include embodiments that include a sensing surface that has two or more sensing elements disposed laterally to each other, where the sensing surface is on a working electrode of an analyte test strip sensor. For example, FIG. 11 shows an exploded perspective view of an analyte sensor test strip, the layers illustrated individually with the electrodes in a first configuration. As shown in FIG. 11, test strip 1100 has a first substrate 1110, a second substrate 1120, and a spacer 1130 positioned therebetween. Test strip 1100 includes at least one working electrode 1140 and at least one counter electrode 1160. The working electrode 1140 is present on a surface of the first substrate 1110 and the counter electrode 1160 is present on a surface of the second substrate 1120 opposing the surface of the first substrate 1110 in a facing relationship with the surface of the first substrate. The working electrode 1140 has an array of sensing elements 1150 disposed on the sensing surface of the working electrode 1140. Test strip 1100 is a layered construction, in certain embodiments having a generally rectangular shape, e.g., its length is longer than its width, although other shapes are possible as well. Another embodiment of a test strip is illustrated in FIG. 12, which shows an exploded perspective view of an analyte sensor test strip, the layers illustrated individually with the electrodes in a second configuration. As shown in FIG. 12, test strip 1200 has a first substrate 1210, a second substrate 1220, and a spacer 1230 positioned therebetween. Test strip 1200 includes at least one working electrode 1240 and at least one counter electrode 1260. The counter electrode 1260 is present on a surface of the first substrate 1210 adjacent the working electrode 1240, such that both the working electrode 1240 and the counter electrode 1260 are present on the surface of the first substrate 1210. The working electrode 1240 has an array of sensing elements 1250 disposed on the sensing surface of the working electrode 1240. Similar to the embodiment shown in FIG. 11, the test strip 1200 shown in FIG. 12 has a layered construction, in certain embodiments having a generally rectangular shape, e.g., its length is longer than its width, although other shapes are possible as well. Additional embodiments of test strips and analyte sensors for use therein are described in more detail in U.S. application Ser. No. 11/281,883, the disclosure of which is incorporated by reference herein in its entirety.

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

Electrochemical Sensors

Embodiments of the present disclosure relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and an in vivo system. In some embodiments, the systems, or at least a portion of the systems, are integrated into a single unit.

A sensor as described herein may be an in vivo sensor or an in vitro sensor (i.e., a discrete monitoring test strip). Such a sensor can be formed on a substrate, e.g., a substantially planar substrate. In certain embodiments, the sensor is a wire, e.g., a working electrode wire inner portion with one or more other electrodes associated (e.g., on, including wrapped around) therewith. The sensor may also include at least one counter electrode (or counter/reference electrode) and/or at least one reference electrode or at least one reference/counter electrode.

Accordingly, embodiments include analyte monitoring devices and systems that include an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time $t_0$, the rate of change of the analyte, etc. Predictive alarms may notify the user of a predicted analyte level that may be of concern in advance of the user's analyte level reaching the future predicted analyte level. This provides the user an opportunity to take corrective action.

FIG. 1 shows a data monitoring and management system such as, for example, an analyte (e.g., glucose) monitoring system 100 in accordance with certain embodiments. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 100 includes an analyte sensor 101, a data processing unit 102 connectable to the sensor 101, and a primary receiver unit 104. In some instances, the primary receiver unit 104 is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link 107, which may optionally be configured for bi-directional communication. Further, the data processing unit 102 may include a transmitter or a transceiver to transmit and/or receive data to and/or from the primary receiver unit 104 and/or the data processing terminal 105 and/or optionally a secondary receiver unit 106.

Also shown in FIG. 1 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. In certain embodiments, the secondary receiver unit 106 may be configured for bi-directional wireless communication with each of the primary receiver unit 104 and the data processing terminal 105. As discussed in further detail below, in some instances, the secondary receiver unit 106 may be a de-featured receiver as compared to the primary receiver unit 104, for instance, the secondary receiver unit 106 may include a limited or minimal number of functions and features as compared with the primary receiver unit 104. As such, the secondary receiver unit 106 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 104. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element, such as an adhesive or the like, to secure it to the user's body. A mount (not shown) attachable to the user and mateable with the data processing unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In some embodiments, the sensor 101 or the data processing unit 102 or a combined sensor/data processing unit may be wholly implantable under the skin surface of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 including data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include a drug delivery device (e.g., an infusion device), such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer an appropriate drug (e.g., insulin) to users, for example, for administering and modifying basal profiles, as well as for determining appropriate boluses for administration based on, among others, the detected analyte levels received from the data processing unit 102. An infusion device may be an external device or an internal device, such as a device wholly implantable in a user.

In certain embodiments, the data processing terminal 105, which may include an infusion device, e.g., an insulin pump, may be configured to receive the analyte signals from the data processing unit 102, and thus, incorporate the functions of the primary receiver unit 104 including data processing for managing the user's insulin therapy and analyte monitoring. In certain embodiments, the communication link 103, as well as one or more of the other communication interfaces shown in FIG. 1, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 2:
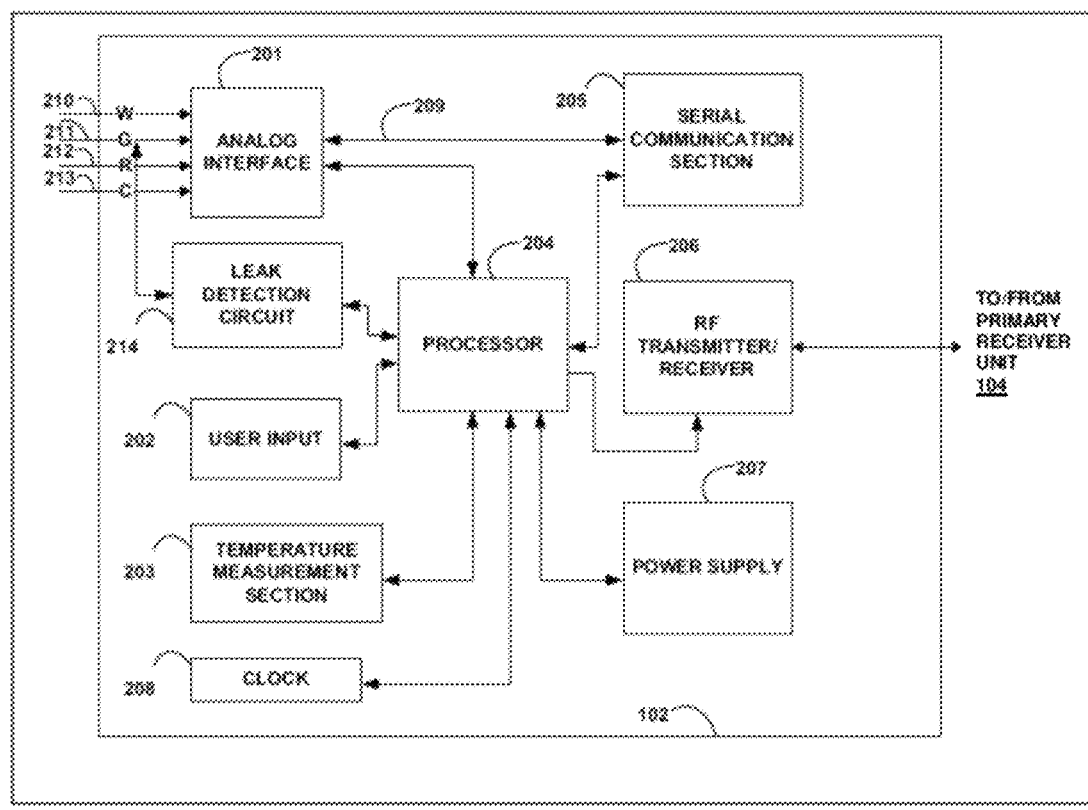
FIG. 2 shows a block diagram of an embodiment of a data processing unit of the analyte monitoring system shown in FIG. 1.

FIG. 2 shows a block diagram of an embodiment of a data processing unit 102 of the analyte monitoring system shown in FIG. 1. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 2, the analyte sensor 101 (FIG. 1) includes four contacts, three of which are electrodes: a work electrode (W) 210, a reference electrode (R) 212, and a counter electrode (C) 213, each operatively coupled to the analog interface 201 of the data processing unit 102. This embodiment also shows an optional guard contact (G) 211. Fewer or greater electrodes may be employed. For example, the counter and reference electrode functions may be served by a single counter/reference electrode. In some cases, there may be more than one working electrode and/or reference electrode and/or counter electrode, etc.

Figure 3:
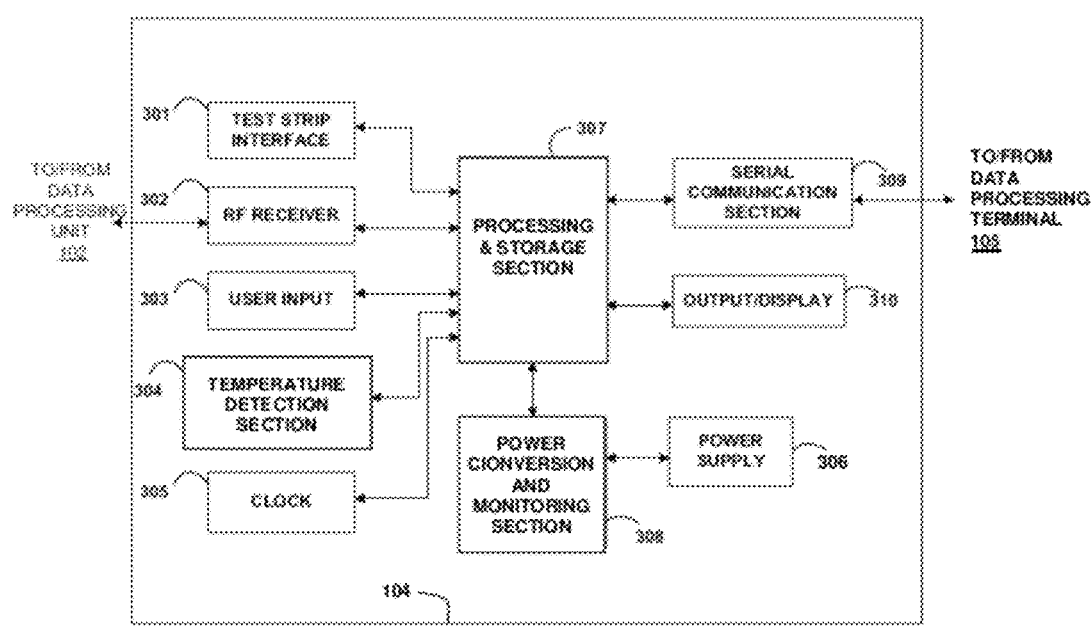
FIG. 3 shows a block diagram of an embodiment of the primary receiver unit of the analyte monitoring system of FIG. 1.

FIG. 3 is a block diagram of an embodiment of a receiver/monitor unit such as the primary receiver unit 104 of the analyte monitoring system shown in FIG. 1. The primary receiver unit 104 includes one or more of: a test strip interface 301, an RF receiver 302, a user input 303, an optional temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output 310, each operatively coupled to the processing and storage section 307. The primary receiver unit 104 may include user input and/or interface components or may be free of user input and/or interface components.

In certain embodiments, the test strip interface 301 includes an analyte testing portion (e.g., a glucose level testing portion) to receive a blood (or other body fluid sample) analyte test or information related thereto. For example, the test strip interface 301 may include a test strip port to receive a test strip (e.g., a glucose test strip). The device may determine the analyte level of the test strip, and optionally display (or otherwise notice) the analyte level on the output 310 of the primary receiver unit 104. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., Freestyle® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 101, confirm results of sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 106, and/or the data processing terminal/infusion device 105 may be configured to receive the analyte value wirelessly over a communication link from, for example, a blood glucose meter. In further embodiments, a user manipulating or using the analyte monitoring system 100 (FIG. 1) may manually input the analyte value using, for example, a user interface (for example, a keyboard, keypad, voice commands, and the like) incorporated in one or more of the data processing unit 102, the primary receiver unit 104, secondary receiver unit 106, or the data processing terminal/infusion device 105.

Additional detailed descriptions are provided in U.S. Pat. Nos. 5,262,035; 5,264,104; 5,262,305; 5,320,715; 5,593,852; 6,175,752; 6,650,471; 6,746,582, and 7,811,231, each of which is incorporated herein by reference in their entirety.

Figure 4:
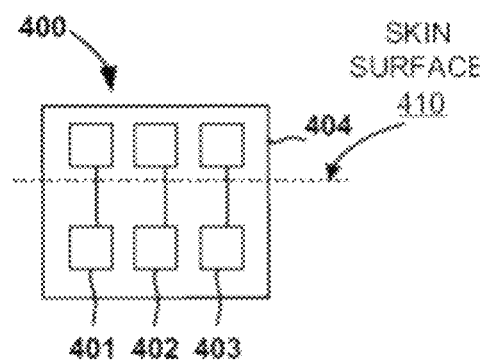
FIG. 4 shows a schematic diagram of an embodiment of an analyte sensor according to the embodiments of the present disclosure.

FIG. 4 schematically shows an embodiment of an analyte sensor 400 in accordance with the embodiments of the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 400 may be wholly implantable in a user or may be configured so that only a portion is positioned within (internal) a user and another portion outside (external) a user. For example, the sensor 400 may include a first portion positionable above a surface of the skin 410, and a second portion positioned below the surface of the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an analyte sensor 500 having a first portion (which in this embodiment may be characterized as a major portion) positionable above a surface of the skin 510, and a second portion (which in this embodiment may be characterized as a minor portion) that includes an insertion tip 530 positionable below the surface of the skin, e.g., penetrating through the skin and into, e.g., the subcutaneous space 520, in contact with the user's biofluid, such as interstitial fluid. Contact portions of a working electrode 511, a reference electrode 512, and a counter electrode 513 are positioned on the first portion of the sensor 500 situated above the skin surface 510. A working electrode 501, a reference electrode 502, and a counter electrode 503 are shown at the second portion of the sensor 500 and particularly at the insertion tip 530. Traces may be provided from the electrodes at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one embodiment, the sensor 500 (such as the analyte sensor unit 101 of FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing element 508. As described herein, two or more sensing elements may be provided on a sensing surface of the working electrode, where the two or more sensing elements are disposed laterally to each other. For example, FIG. 5C shows a schematic view of a portion of working electrode 501. Working electrode 501 includes a plurality of individual sensing elements 508. The sensing elements 508 are discontiguous, such that the sensing elements 508 are arranged into an array of individual sensing elements 508 on the working electrode 501.

A first insulation layer 505, such as a first dielectric layer in certain embodiments, is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, as described herein having an extended lifetime, which includes a layer of redox polymer as described herein.

A second insulation layer 506, such as a second dielectric layer in certain embodiments, may be disposed or layered on at least a portion of the second conducting layer 509. Further, a third conducting layer 503 may be disposed on at least a portion of the second insulation layer 506 and may provide the counter electrode 503. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer). The embodiments of FIGS. 5A and 5B show the layers having different lengths. In certain instances, some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing therebetween and/or include a dielectric material or insulation material disposed between the conducting layers/electrodes. Furthermore, in certain embodiments, one or more of the electrodes 501, 502, 503 may be disposed on opposing sides of the substrate 504. In such embodiments, contact pads may be one the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing element. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element (see for example sensing element 508 of FIG. 5B) proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

A variety of different sensing element configurations may be used. In certain embodiments, the sensing elements are deposited on the conductive material of a working electrode. The sensing elements may extend beyond the conductive material of the working electrode. In some cases, the sensing elements may also extend over other electrodes, e.g., over the counter electrode and/or reference electrode (or counter/reference is provided). In other embodiments, the sensing elements are contained on the working electrode, such that the sensing elements do not extend beyond the conductive material of the working electrode.

Sensing elements that are in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having sensing elements which contain a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing elements are not deposited directly on the working electrode. Instead, the sensing elements 508 may be spaced apart from the working electrode, and separated from the working electrode, e.g., by a separation layer. A separation layer may include one or more membranes or films or a physical distance. In addition to separating the working electrode from the sensing elements, the separation layer may also act as a mass transport limiting layer and/or an interferent eliminating layer and/or a biocompatible layer.

In certain embodiments which include more than one working electrode, one or more of the working electrodes may not have corresponding sensing elements, or may have sensing elements that do not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing elements by, for example, subtracting the signal.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. This sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the enzyme-containing sensing elements and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. A membrane applied in this manner may have any combination of the following functions: (1) mass transport limitation, i.e., reduction of the flux of analyte that can reach the sensing elements, (2) biocompatibility enhancement, or (3) interferent reduction.

In some instances, the membrane may form one or more bonds with the sensing elements. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, cros slinking of the membrane to the sensing element facilitates a reduction in the occurrence of delamination of the membrane from the sensor.

In certain embodiments, the sensing system detects hydrogen peroxide to infer glucose levels. For example, a hydrogen peroxide-detecting sensor may be constructed in which the sensing elements include an enzyme such as glucose oxidase, glucose dehydrogenase, or the like, and is positioned on the working electrode. The sensing elements may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from sensing elements prepared by combining together, for example: (1) a redox mediator having a transition metal complex including an Os polypyridyl complex with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. Glucose-sensing elements may be constructed by combining together (1) a redox mediator having a transition metal complex including Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a user, then the sensor may be made flexible (although rigid sensors may also be used for implantable sensors) to reduce pain to the user and damage to the tissue caused by the implantation of and/or the wearing of the sensor. A flexible substrate often increases the user's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. An implantable sensor having a rigid substrate may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the user during operation of the sensor. However, the barb is typically small enough so that little damage is caused to the subcutaneous tissue when the sensor is removed for replacement.

An implantable sensor may also, optionally, have an anticlotting agent disposed on a portion of the substrate which is implanted into a user. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping, etc. The anticlotting agent is allowed to dry on the sensor. The anticlotting agent may be immobilized on the surface of the sensor or it may be allowed to diffuse away from the sensor surface. The quantities of anticlotting agent disposed on the sensor may be below the amounts typically used for treatment of medical conditions involving blood clots and, therefore, have only a limited, localized effect.

Insertion Device

An insertion device can be used to subcutaneously insert the sensor into the user. The insertion device is typically formed using structurally rigid materials, such as metal or rigid plastic. Materials may include stainless steel and ABS (acrylonitrile-butadiene-styrene) plastic. In some embodiments, the insertion device is pointed and/or sharp at the tip to facilitate penetration of the skin of the user. A sharp, thin insertion device may reduce pain felt by the user upon insertion of the sensor. In other embodiments, the tip of the insertion device has other shapes, including a blunt or flat shape. These embodiments may be useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a user. The sensor control unit is optionally formed in a shape that is comfortable to the user and which may permit concealment, for example, under a user's clothing. The thigh, leg, upper arm, shoulder, or abdomen are convenient parts of the user's body for placement of the sensor control unit to maintain concealment. However, the sensor control unit may be positioned on other portions of the user's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the user. The housing typically contains most or all of the electronic components of the sensor control unit.

The housing of the sensor control unit may be formed using a variety of materials, including, for example, plastic and polymeric materials, such as rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, including a battery or a speaker for an audible alarm, may be placed in the hollow or recessed areas.

The sensor control unit is typically attached to the skin of the user, for example, by adhering the sensor control unit directly to the skin of the user with an adhesive provided on at least a portion of the housing of the sensor control unit which contacts the skin or by suturing the sensor control unit to the skin through suture openings in the sensor control unit.

When positioned on the skin of a user, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that operate the sensor and the analyte monitoring device system. The electronic components of the sensor control unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit. In some cases, a system may only need to be calibrated once during the manufacturing process, where recalibration of the system is not required.

If necessary, calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care, Alameda, Calif.). For example, test strips that require less than about 1 nanoliter of sample may be used. In certain embodiments, a sensor may be calibrated using only one sample of body fluid per calibration event. For example, a user need only lance a body part one time to obtain a sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a health care professional or by the user. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a sensor. In these embodiments, the processing circuit of the sensor control unit is able to determine a level of the analyte and activate an alarm system if the analyte level exceeds a threshold value. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value of 70 mg/dL for hypoglycemia because the datapoint does not indicate that particular condition as defined by the chosen threshold value.

An alarm may also be activated if the sensor readings indicate a value that is outside of (e.g., above or below) a measurement range of the sensor. For glucose, the physiologically relevant measurement range is typically 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system may be activated if the rate of change in glucose concentration exceeds a threshold value which may indicate that a hyperglycemic or hypoglycemic condition is likely to occur. In some cases, the alarm system is activated if the acceleration of the rate of change in glucose concentration exceeds a threshold value which may indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. patent applications, and/or non-U.S. patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the invention may be applicable will be readily apparent to those of skill in the art to which the invention is directed upon review of the specification. Various aspects and features of the invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the invention may have been described largely with respect to applications, or more specifically, medical applications, involving diabetic humans, it will be understood that such aspects and features also relate to any of a variety of applications involving non-diabetic humans and any and all other animals. Further, although various aspects and features of the invention may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the invention have been described with respect to various embodiments and specific examples herein, all of which may be made or carried out conventionally, it will be understood that the invention is entitled to protection within the full scope of the appended claims.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Figure 6:
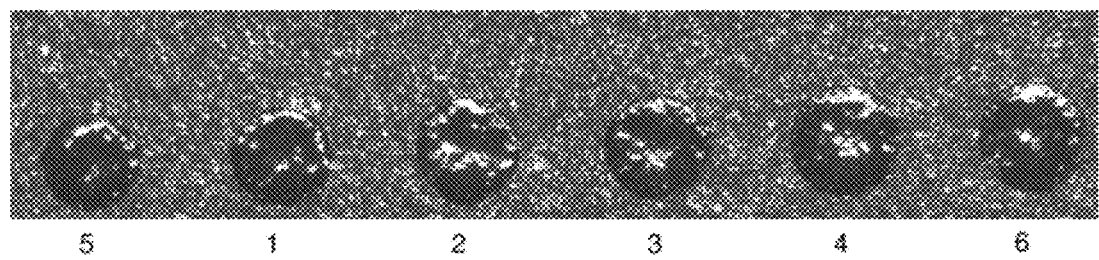
FIG. 6 shows a photograph of a working electrode coated with six sensing elements with a radius of approximately 150 µm each at a distance of approximately 150 µm from each other. The resulting sensors have a coefficient of variation in sensitivity of 5% or less.

FIG. 6 shows a photograph of a working electrode coated with six sensing elements (labeled 1 to 6) with a radius of approximately 150 μm each at a distance of approximately 150 μm from each other. The resulting sensors have a coefficient of variation in sensitivity of 5% or less. The diameters of each sensing element in FIG. 6 are shown in Table 1 below.

TABLE 1

| Sensing Element | Diameter (μm) |
|---|---|
| 1 | 146.85 |
| 2 | 156.50 |
| 3 | 153.91 |
| 4 | 165.58 |

TABLE 1-continued

| Sensing Element | Diameter (μm) |
|---|---|
| 5 | 145.04 |
| 6 | 166.89 |

Example 2

FIG. 10 shows a graph of current (μA) vs. time (seconds) for a sensing layer formulation deposited as an array of small sensing elements (9 pL/droplet), and a sensing layer formulation deposited as a stripe coating on the surface of a gold working electrode. The sensor with the sensing layer formulation deposited as an array of small sensing elements recovered 26% more charge than the stripe-coated sensor under the same test conditions.

That which is claimed is:

1. A plurality of analyte sensors each comprising:
a working electrode comprising a conductive material disposed on a substrate;
a counter electrode;
a sensing surface disposed on the conductive material of the working electrode, the sensing surface comprising two or more discontiguous sensing elements arranged thereon,
wherein each discontiguous sensing element has an arcuate cross-sectional profile and semi-spherical shape, a diameter of 50 μm to 175 μm, a volume of 0.1 to 50 pico liters, and comprises an analyte-responsive enzyme; and
a flux limiting membrane that covers the discontiguous sensing elements and is in contact with the working electrode between each discontiguous sensing element; and
a sensor control unit comprising a processing circuit,
wherein the sensor control unit comprising a processing circuit is configured to process factory-determined calibrated measurements that are input or stored in the sensor control unit, such that the plurality of analyte sensors are thereby factory calibrated, requiring no user calibration or recalibration.

2. The plurality of analyte sensors of claim 1, wherein the discontiguous sensing elements are arranged as individual sensing elements on the working electrode.

3. The plurality of analyte sensors of claim 2, wherein the sensing surface comprises an array of two or more individual sensing elements.

4. The plurality of analyte sensors of claim 3, wherein the sensing surface comprises an array of 100 or more individual sensing elements.

5. The plurality of analyte sensors of claim 1, wherein the sensing surface has a density of discontiguous sensing elements ranging from 2-1000 sensing elements/mm$^2$.

6. The plurality of analyte sensors of claim 1, wherein the sensing surface further comprises inter-feature areas.

7. The plurality of analyte sensors of claim 6, wherein the inter-feature areas surround the discontiguous sensing elements.

8. The plurality of analyte sensors of claim 6, wherein the discontiguous sensing elements have an inter-feature distance ranging from 1 μm to 500 μm.

9. The plurality of analyte sensors of claim 6, wherein the inter-feature areas are free of the analyte-responsive enzyme.

10. The plurality of analyte sensors of claim 6, wherein the inter-feature areas are free of a redox mediator.

11. The plurality of analyte sensors of claim 1, wherein the two or more discontiguous sensing elements are a first layer, and further comprising a second layer of two or more discontiguous sensing elements disposed on first layer.

12. The plurality of analyte sensors of claim 1, wherein at least a portion of the plurality of analyte sensors is adapted to be subcutaneously positioned in a subject.

13. The plurality of analyte sensors of claim 1, wherein the analyte-responsive enzyme comprises a glucose-responsive enzyme.

14. The plurality of analyte sensors of claim 13, wherein the sensing elements comprise a redox mediator.

15. The plurality of analyte sensors of claim 14, wherein the redox mediator comprises a ruthenium-containing complex or an osmium-containing complex.

16. The plurality of analyte sensors of claim 13, wherein the plurality of analyte sensors are glucose sensors.

17. The plurality of analyte sensors of claim 13, wherein the plurality of analyte sensors are in vivo sensors.

18. The plurality of analyte sensors of claim 13, wherein the plurality of analyte sensors are in vitro sensors.

19. The plurality of analyte sensors of claim 1, wherein each discontiguous sensing element further element comprises: a polymer; and a redox mediator covalently bonded to the polymer.

20. The method of claim 1, wherein each discontiguous sensing element further comprises: a polymer; and a redox mediator.

21. The plurality of analyte sensors of claim 1, wherein the plurality of analyte sensors achieve a coefficient of variation in sensitivity of less than 20% therebetween.

22. A method comprising:
monitoring a level of an analyte with at least a portion of at least one of a plurality of analyte sensors configured to be positioned into skin of a subject, wherein the plurality of analyte sensors each comprises:
a working electrode comprising a conductive material disposed on a substrate;
a counter electrode;
a sensing surface disposed on the conductive material of the working electrode, the sensing surface comprising two or more discontiguous sensing elements arranged thereon,
wherein each discontiguous sensing element has an arcuate cross-sectional profile and semi-spherical shape, a diameter of 50 μm to 175 μm, a volume of 0.1 to 50 pico liters, and comprises an analyte-responsive enzyme; and
a flux limiting membrane that covers the discontiguous sensing elements and is in contact with the working electrode between each discontiguous sensing element; and
a sensor control unit comprising a processing circuit, wherein the sensor control unit comprising a processing circuit is configured to process factory-determined calibrated measurements that are input or stored in the sensor control unit, such that the plurality of analyte sensors are thereby factory calibrated, requiring no user calibration or recalibration; and
determining a level of an analyte over a period of time from signals generated by the analyte sensor.

23. The method of claim 22, wherein the plurality of analyte sensors achieve a coefficient of variation in sensitivity of less than 20% therebetween.

24. The method of claim 22, wherein the discontiguous sensing elements are arranged as individual sensing elements on the working electrode.

25. The method of claim 24, wherein the sensing surface comprises an array of two or more individual sensing elements.

26. The method of claim 25, wherein sensing surface comprises an array of 100 or more individual sensing elements.

27. The method of claim 22, wherein the sensing surface has a density of discontiguous sensing elements ranging from 2-1000 sensing elements/mm$^2$.

28. The method of claim 23, wherein the sensing surface further comprises inter-feature areas.

29. The method of claim 28, wherein the inter-feature areas surround the discontiguous sensing elements.

30. The method of claim 28, wherein the sensing elements have an inter-feature distance ranging from 1 μm to 500 μm.

31. The method of claim 28, wherein the inter-feature areas are free of the analyte-responsive enzyme.

32. The method of claim 28, wherein the inter-feature areas are free of a redox mediator.

33. The method of claim 22, wherein the two or more discontiguous sensing elements are a first layer, and further comprising a second layer of two or more sensing elements disposed on the first layer.

34. The method of claim 22, wherein at least a portion of at least one of the plurality of analyte sensors is adapted to be subcutaneously positioned in a subject.

35. The method of claim 22, wherein the analyte-responsive enzyme comprises a glucose-responsive enzyme.

36. The method of claim 35, wherein the discontiguous sensing elements comprise a redox mediator.

37. The method of claim 35, wherein the at least one of a plurality of analyte sensors is a glucose sensor.

* * * * *